(12) United States Patent
Sukawa et al.

(10) Patent No.: US 7,942,800 B2
(45) Date of Patent: May 17, 2011

(54) CENTRIFUGAL SEPARATOR AND ANALYZER PROVIDED WITH SAME

(75) Inventors: Yukihiro Sukawa, Kyoto (JP); Yukio Higashiisogawa, Kyoto (JP)

(73) Assignee: Arkray, Inc. (JP)

( * ) Notice: Subject to any disclaimer, the term of this patent is extended or adjusted under 35 U.S.C. 154(b) by 1027 days.

(21) Appl. No.: 11/666,139

(22) PCT Filed: Oct. 25, 2005

(86) PCT No.: PCT/JP2005/019556
§ 371 (c)(1),
(2), (4) Date: Apr. 23, 2007

(87) PCT Pub. No.: WO2006/046437
PCT Pub. Date: May 4, 2006

(65) Prior Publication Data
US 2007/0248492 A1  Oct. 25, 2007

(30) Foreign Application Priority Data
Oct. 28, 2004  (JP) .................................. 2004-313965

(51) Int. Cl.
*B04B 5/02* (2006.01)
(52) U.S. Cl. .......................................................... 494/20
(58) Field of Classification Search ................ 494/4, 16, 494/20; 422/72
See application file for complete search history.

(56) References Cited

U.S. PATENT DOCUMENTS

| 4,342,419 A | * | 8/1982 | Conway ........................... 494/20 |
| 7,150,858 B2 | | 12/2006 | Matsuda et al. |
| 2003/0185710 A1 | * | 10/2003 | Matsuda et al. ................. 422/72 |
| 2003/0199382 A1 | * | 10/2003 | Moscone, Sr. ................... 494/20 |

FOREIGN PATENT DOCUMENTS

| JP | 53-131567 | 11/1978 |
| WO | WO 02/016043 | 2/2002 |

OTHER PUBLICATIONS

International Search Report from corresponding PCT/JP2005-019556, mailed Jan. 24, 2006.

* cited by examiner

*Primary Examiner* — Walter D Griffin
*Assistant Examiner* — Timothy Cleveland
(74) *Attorney, Agent, or Firm* — Studebaker & Brackett PC; Donald R. Studebaker (57) ABSTRACT

The present invention relates to a centrifugal separator (5) including a rotor (51) which pivotally supports a container (9) including an upper opening (90B) and which is to be rotated to apply a centrifugal force to the container (9). The rotor (51) includes an evaporation preventer (55A) for preventing separation target liquid contained in the container (9) from evaporating when the rotor (51) is rotated. The evaporation preventer (55A) includes a standing wall (55Ab) which is positioned in front of the upper opening (90B) when the container (9) is pivoted by rotating the rotor (51).

22 Claims, 11 Drawing Sheets

CENTRIFUGAL SEPARATOR AND ANALYZER PROVIDED WITH SAME

TECHNICAL FIELD

The present invention relates to a centrifugal separator and an analytical apparatus provided with a centrifugal separator.

BACKGROUND ART

In a blood test, the number (concentration) of red or white blood cells in the blood may be measured together with the concentration of other components such as glucose, albumin and calcium. The concentration measurement of such components is performed by an optical method. Specifically, the measurement is performed by applying a sample onto a reagent pad of a test piece having been impregnated with an appropriate reagent, and then determining the degree of the color development based on the reflection of light from the reagent pad. The number of blood cells varies between individuals. Thus, in measuring the concentration of a component other than the blood cells, it is necessary to avoid the measurement error due to the blood cell components. Accordingly, in such measurement, the whole blood is subjected to centrifugal separation to cause the blood cell components to precipitate, and then the supernatant fluid is applied to the reagent pad as the sample.

To automatically perform such measurement, an analytical apparatus incorporating a centrifugal separator has been proposed (e.g. Patent Document 1). The centrifugal separator of the analytical apparatus disclosed in this document performs centrifugal separation with a container mounted to a rotor. In this analytical apparatus, when the container is rotated, air flow is generated in the container, so that the liquid retained in the container evaporates. When the liquid retained in the container evaporates, the amount of liquid (the concentration of the detection target component in the liquid) changes to result in a measurement error. To prevent the liquid from evaporating, a container provided with a lid is often used.

However, the provision of a lid for a container increases the number of parts and the material cost. Further, the step of mounting a lid to a container deteriorates the efficiency of the manufacturing process. Since the lid of the container is provided for preventing the liquid in the container from evaporating, it is desirable to make the opening diameter of the lid as small as possible within the range in which a nozzle of a pipette unit can be inserted. Therefore, to take the liquid after centrifugal separation by using a pipette unit, it is necessary to accurately position the opening of the lid. As a result, the structure of the apparatus becomes complicated, so that the manufacturing cost increases.

Patent Document 1: PCT WO02/016043

DISCLOSURE OF THE INVENTION

An object of the present invention is to provide a technique for performing cost-effective centrifugal separation.

According to a first aspect of the present invention, there is provided a centrifugal separator comprising a rotor which pivotally supports at least one container including an upper opening and which is to be rotated for applying a centrifugal force to the container. The rotor is provided with an evaporation preventer for preventing separation target liquid contained in the container from evaporating when the rotor is rotated.

According to a second aspect of the present invention, there is provided an analytical apparatus for analyzing at least one component contained in a sample, where the analytical apparatus comprises a centrifugal separator for separating a solid component contained in the sample from a liquid component. The centrifugal separator includes a rotor which pivotally supports at least one container including an upper opening and which is to be rotated to apply a centrifugal force to the container. The rotor is provided with an evaporation preventer for preventing separation target liquid contained in the container from evaporating when the rotor is rotated.

The evaporation preventer controls air flow around the container when the rotor supporting the container is rotated. Preferably, the evaporation preventer includes a standing wall which is positioned in front of the upper opening when the container is pivoted by rotating the rotor.

The standing wall may be formed integral with the rotor. The standing wall may be movable in a radial direction of the rotor. In this case, when the rotor is rotated, the standing wall moves outward in the radial direction due to a centrifugal force.

The evaporation preventer may comprise a peripheral wall which is positioned on a periphery of the upper opening of the container when the container is pivoted by rotating the rotor. The peripheral wall may include an upper wall extending from an upper portion of the standing wall outward in the radial direction of the rotor. The peripheral wall may include a lower wall positioned lower than the upper wall and extending from the standing wall outward in the radial direction of the rotor. The upper wall and the lower wall do not necessarily need to be formed integrally on the standing wall.

The evaporation preventer further comprises a pair of side walls which are positioned on the periphery of the upper opening when the container is pivoted by rotating the rotor and which project upward. For instance, the paired side walls are connected to opposite ends of the standing wall. For instance, each of the side walls includes an engagement portion for coming into engagement with a pivot shaft of the container in supporting the container.

The rotor is capable of supporting a container and has a center of gravity which is offset from the rotation axis of the rotor when the rotor is not supporting the container, and wherein the center of gravity of the rotor and the container in all is located on the rotation axis when the rotor is rotated at a predetermined rotation speed and the container is pivoted through a predetermined angle, with a predetermined amount of separation target liquid retained in the container.

BRIEF DESCRIPTION OF THE DRAWINGS

FIG. 11A is a bottom view showing another example of rotor, whereas

FIG. 12 is a bottom view for describing the operation of the rotor shown in FIGS. 11A and 11B, whereas

BEST MODE FOR CARRYING OUT THE INVENTION

FIGS. 1-4 show an analytical apparatus 1 designed to measure the concentration of a particular component in blood by using test pieces 2A and 2B. The analytical apparatus includes a housing 3, a test piece table 4, a centrifugal separator 5, a positioning mechanism 6, a pipette unit 7 and a photometry mechanism 8.

Figure 1:
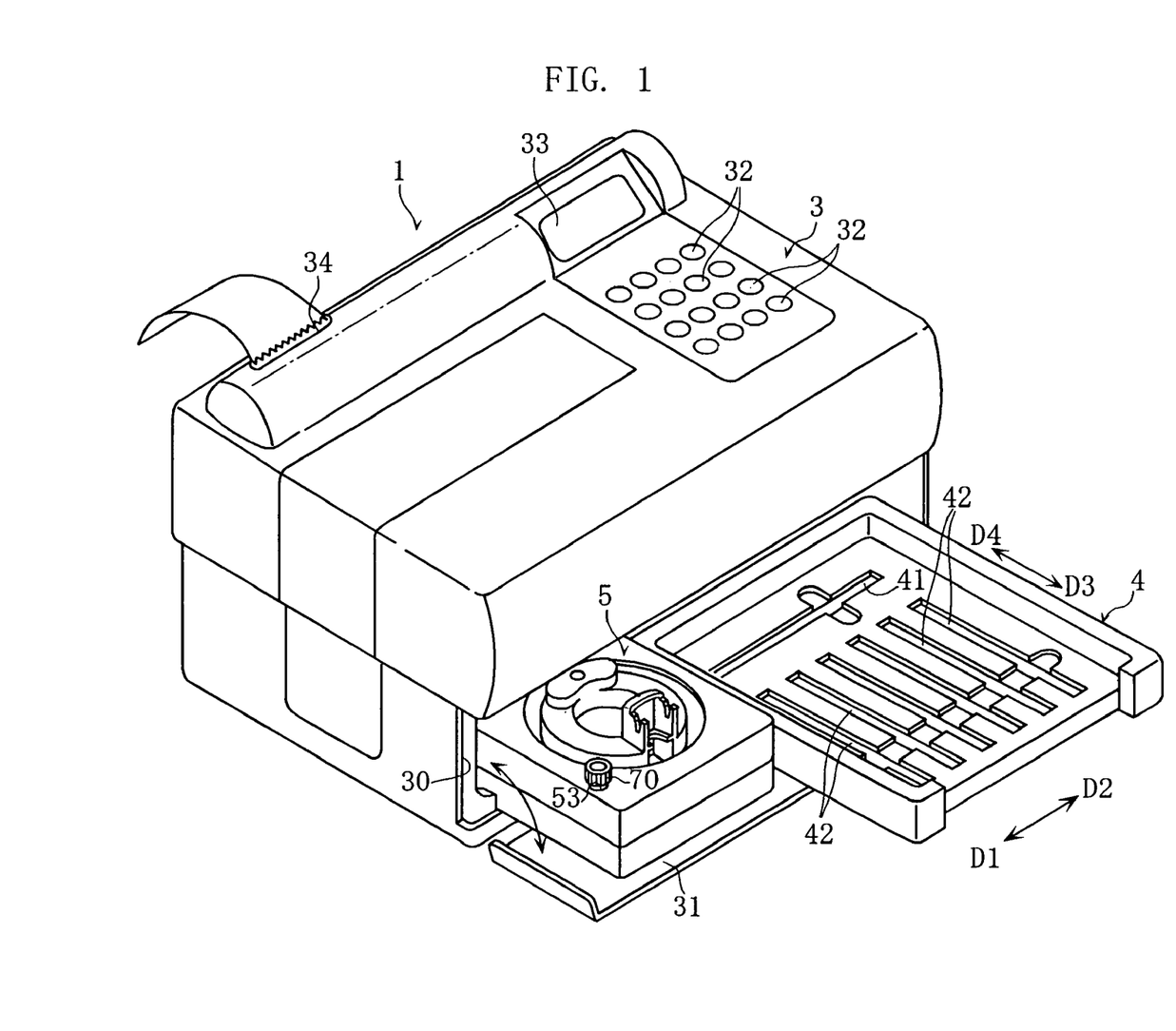
FIG. 1 is an overall perspective view showing an example of analytical apparatus according to the present invention.

As better shown in FIG. 1, the housing 3 defines the appearance of the analytical apparatus 1 and accommodates various elements. The housing includes an opening 30 at the front side thereof. The opening 30 is selectively opened or closed by a lid 31. When the opening 30 is opened, the inside and the outside of the housing 3 communicate with each other. In this way, it is possible to select the state in which the test piece table 4 and the centrifugal separator 5 are accommodated in the housing 3 or the state in which most part of these members are exposed outside the housing 3 (See FIG. 2).

The housing 3 has an upper surface provided with various operation buttons 32 and a display 33 on the right side thereof and a recording paper discharge port 34 on the left side of the rear portion. The operation buttons 32 are utilized for setting measurement conditions and controlling the operation of the analytical apparatus 1. The display 33 displays the measurement results and the operation results of the operation buttons 32, for example.

Figure 2:
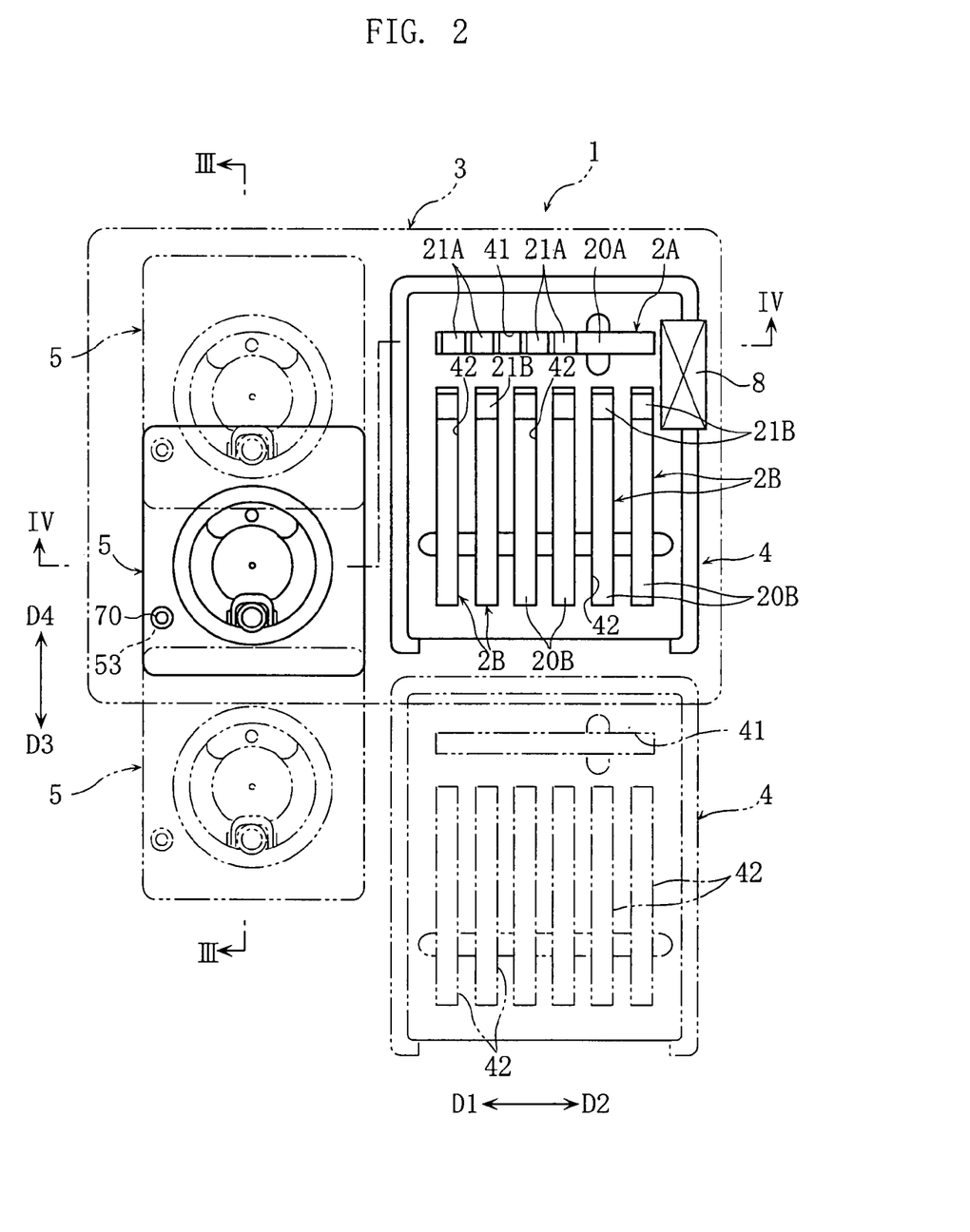
FIG. 2 is a plan view showing an internal structure of the analytical apparatus of FIG. 1.

As shown in FIGS. 1 and 2, the test piece table 4 is utilized for placing test pieces 2A and 2B and formed with a first slit 41 and a plurality of (six in this embodiment) second slits 42.

The first slit 41 extends in the direction indicated by arrows D1, D2 of the housing 3 and serves to hold a test piece 2A for multi-component measurement. The test piece 2A for multi-component measurement comprises a substrate 20A in the form of a strip and a plurality of (five in this embodiment) reagent pads 21A aligned on the substrate in the longitudinal direction of the substrate. Each of the reagent pads 21A contains a reagent which develops a color upon reaction with a particular component such as glucose, albumin or calcium.

Each of the second slits 42 extends in the direction indicated by arrows D3, D4 of the housing 3 and serves to hold a test piece 2B for single-component measurement. The test piece 2B for single-component measurement comprises a substrate 20B in the form of a strip and a single reagent pad 21B provided on the substrate. The reagent pad 21B contains a reagent which develops a color upon reaction with a particular component such as glucose, albumin or calcium.

The test piece table 4 is made movable in the direction of arrows D3, D4 relative to the housing 3 by a known mechanism. Specifically, in placing or removing the test piece 2A, 2B on or from the test piece table, the test piece table 4 is set at a position where the first and the second slits 41 and 42 are exposed outside of the housing 3. In performing photometry with respect to the reagent pads 21A, 21B, the test piece table 4 is set at a position where the first and the second slits 41 and 42 are accommodated in the housing 3.

Figure 3:
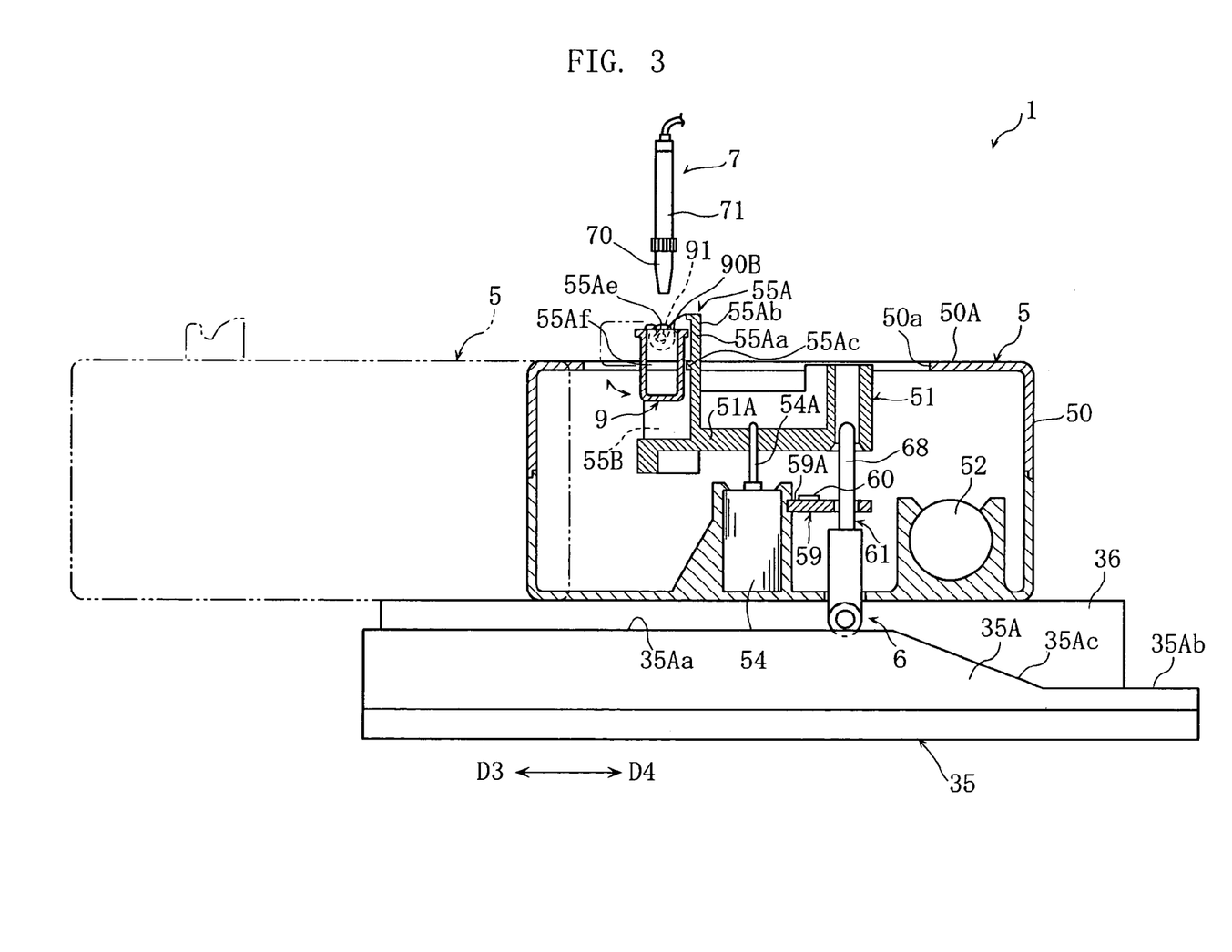
FIG. 3 is a sectional view taken along lines III-III in FIG. 2.
Figure 4:
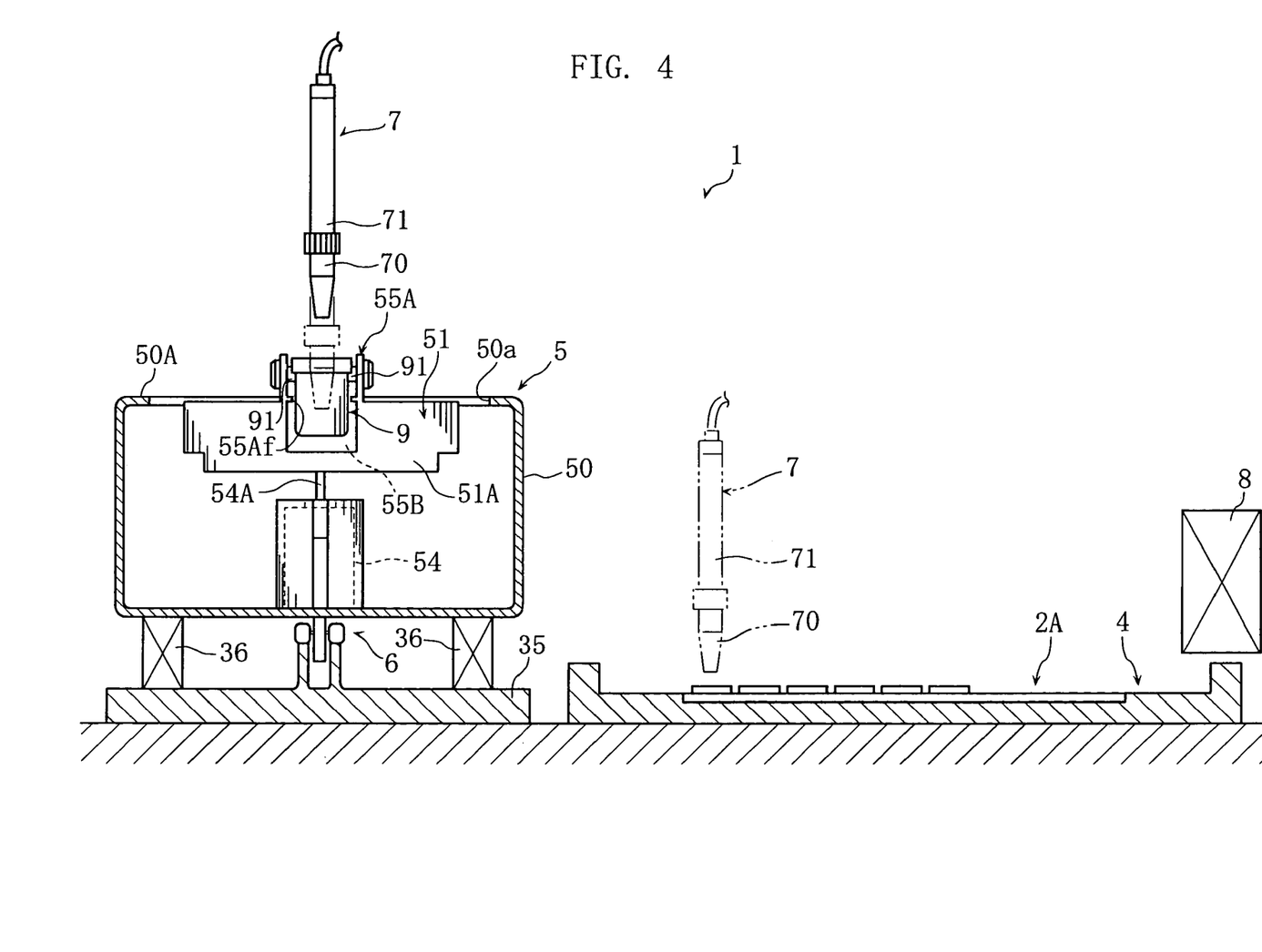
FIG. 4 is a sectional view taken along lines IV-IV in FIG. 2.

As shown in FIGS. 3 and 4, the centrifugal separator 5 is utilized for separating solid components (e.g. blood cell components) from the blood retained in a container 9. The centrifugal separator 5 includes a casing 50 and a rotor 51.

The casing 50 serves to accommodate various elements and move the elements collectively. By the use of a known driving mechanism 36, the casing 50 is reciprocally movable on the table 35 in the direction of the arrows D3, D4. Since the casing 50 is reciprocally movable in the direction of the arrows D3, D4, the centrifugal separator 5 (rotor 51) can be selectively exposed in front of the housing 3 or accommodated in the housing 3 (See FIG. 2). For instance, as the driving mechanism 36, a rack and pinion mechanism may be employed. When a rack and pinion mechanism is employed as the driving mechanism 36, a pinion gear (now shown) integrally provided at the casing 50 is driven for rotation by a motor 52 arranged in the casing 50, and the pinion gear meshes with a rack (not shown) to move the casing 50 reciprocally.

Figure 7:
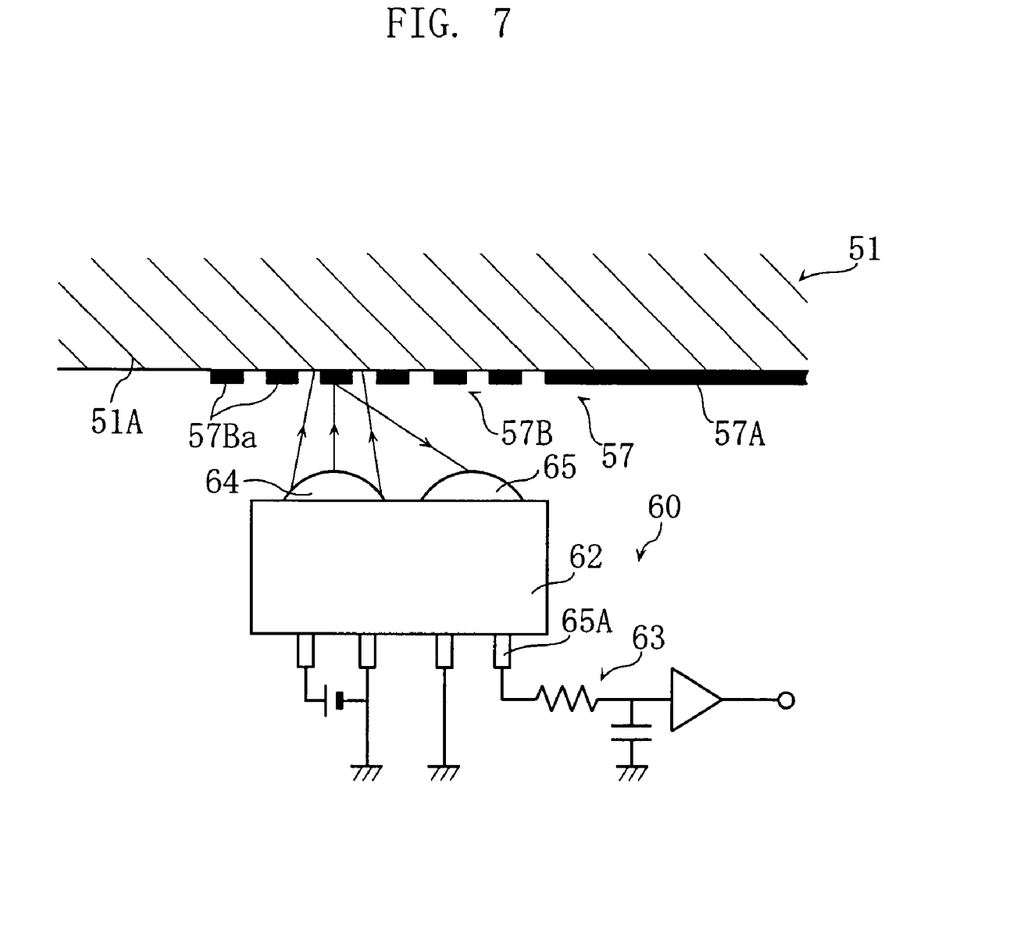
FIG. 7 is a schematic view of a detector of an analytical apparatus.

The casing 50 includes an upper wall 50A formed with a through-hole 50a. The through-hole 50a is provided for allowing the rotation of the rotor 51 and the mounting and detachment of the container 9 relative to the rotor 51. The upper wall 50A is provided with a tip setting portion 53 for holding a tip 70 to be mounted to the pipette unit 7 (See FIGS. 3 and 4), as shown in FIG. 7.

As shown in FIGS. 3 and 4, a motor 54 is arranged in the casing 50 at a position directly below the through-hole 50a. The motor 54 applies a rotational force to the rotor 51 and includes a rotating shaft 54A supported by a bottom wall 51A of the rotor 51. The rotational output of the motor 54A is transmitted to the rotor 51 via the rotating shaft 54A, whereby the rotor 51 is driven for rotation.

As shown in FIGS. 3-6, the rotor 51 applies a centrifugal force to the blood contained in the container 9 and includes a container holder 55, a projection 56, a detection target portion 57 and an engagement hole 58. The container 9 includes a container body 90 including an accommodation space 90A and an upper opening 90B, a pair of shaft portions 91 projecting laterally from an upper portion of the container body 90, and a stopper 92 provided at an end of each of the shaft portions 91.

Figure 5:
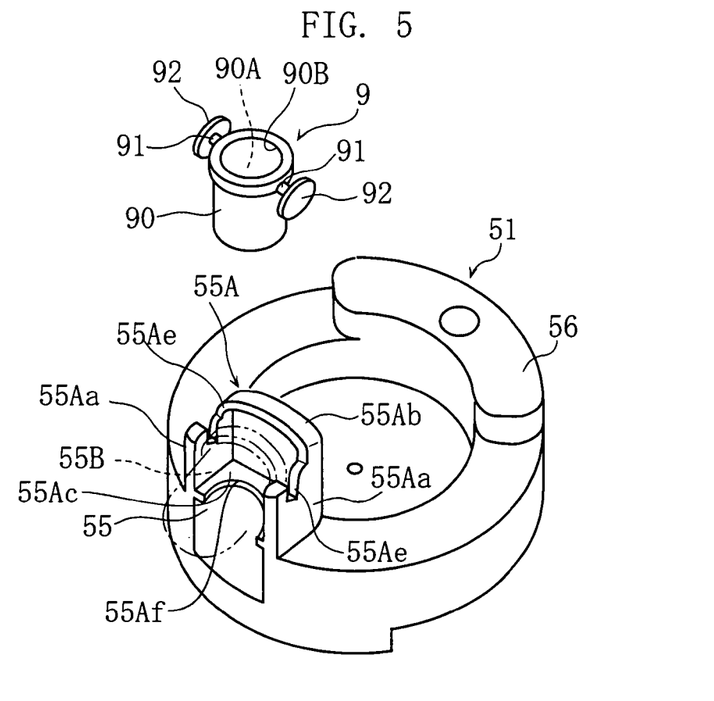
FIG. 5 is an overall perspective view showing a rotor and a container of a centrifugal separator of the analytical apparatus shown in FIG. 1.

The container holder 55 serves to hold the container 9 and includes a support wall 55A and an accommodation space 55B.

The support wall 55A is utilized for holding the container 9 and controlling the air flow around the container 9 when the rotor 51 is rotated. The support wall 55A includes two side walls 55Aa, a deeper wall 55Ab, an upper wall 55Ac and a lower wall 55Ad and entirely projects upward from the upper surface of the rotor 51. The two side walls 55Aa are connected to opposite ends of the deeper wall 55Ab and spaced from each other by a constant distance. Each of the side walls 55Aa is formed with a cutout 55Ae for receiving the shaft portion 91 of the container 9. When the shaft portions 91 are received in the cutouts 55Ae, the container 9 is surrounded by the two side walls 55Aa and the deeper wall 55Ab, and the container 9 is pivotable about the shaft portions 91. The deeper wall 55Ab is positioned in front of the upper opening 90B of the container 9 when the rotor 51 is rotated. The upper wall 55Ac and the lower wall 55Ad are positioned on the periphery of the upper opening 90B of the container 9 when the rotor 51 is rotated. The upper wall 55Ac extends from the upper end of the deeper wall 55Ab radially outwardly of the rotor 51 so as to bridge the two side walls 55Aa. The lower wall 55Ad is positioned lower than the upper wall 55Ad and extends from the deeper wall 55Ab radially outwardly of the rotor 51 so as to bridge the two side walls 55Aa. The lower wall 55Ad is formed with an arcuate cutout 55Af. The cutout 55Af is provided for preventing the container 9 from coming into contact with the lower wall 55Ad when the shaft portions 91 of the container 9 are received in the cutouts 55Ae. By the provision of the cutout 55Af, the container 9 can be suspended while having an appropriate posture.

The accommodation space 55B serves to accommodate the container 9 with the shaft portions 91 of the container 9 received in the cutouts 55Ae of the support wall 55A and allows the pivotal movement of the container 9. The accommodation space is open radially outwardly of the rotor 51. The accommodation space 55B is defined by the support wall 55A and an opening formed at the rotor 51.

The container 9 held by the container holder 55 can be pivoted upward by rotating the rotor 51 and applying a centrifugal force to the container. As shown in FIG. 5, when the container pivots, the deeper wall 55Ab of the support wall 55A is positioned in front of the upper opening 90B of the container 9. Therefore, the flow of air into the container 9 through the upper opening 90B can be suppressed. Further, since the two side walls 55Aa, the upper wall 55Ac and the lower wall 55Ad of the support wall 55A are positioned on the periphery of the opening 90B of the container 9, the flow of air into the container 9 is further suppressed.

When the rotor 51 is rotated at a predetermined rotation speed with the container 9 containing an appropriate amount of blood held by the container holder 55, the projection 56 serves to keep the balance so that the center of gravity of the rotor 51 and the container 9 in all is positioned on the rotation axis of the rotor 51.

As shown in FIG. 3, the engagement hole 58 constitutes a positioning mechanism 6, which will be described later, and serves to fix the position of the rotor 51 by inserting a pin 68 of a stopper 61 of the positioning mechanism 6 into the engagement hole. The engagement hole 58 vertically penetrates the rotor 51 at a position offset from the rotation axis of the rotor and flares downward to facilitate the insertion of the stopper 61.

Figure 6:
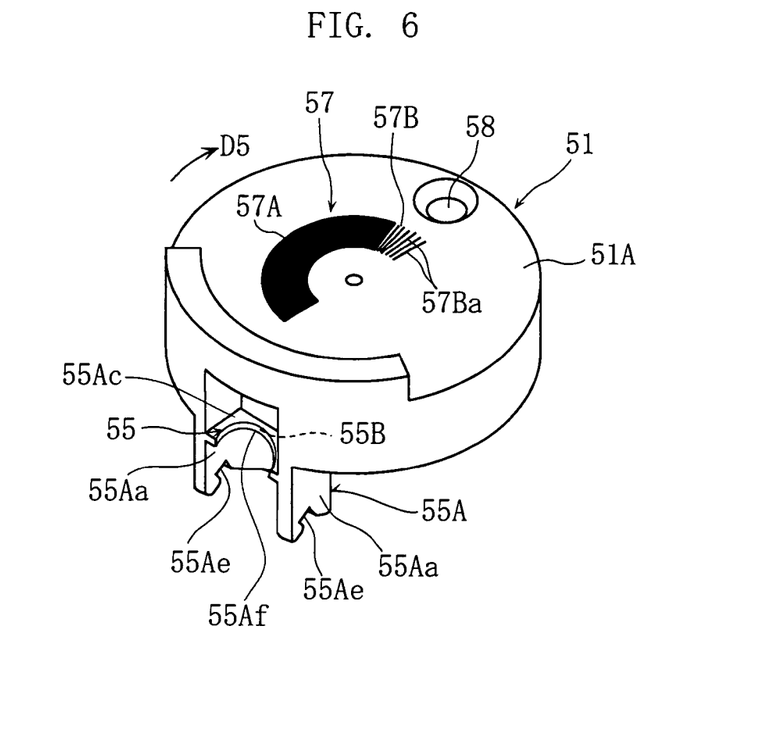
FIG. 6 is an overall perspective view of the rotor of FIG. 5 as viewed from the reverse surface side.

As shown in FIG. 6, the detection target portion 57, which is utilized for detecting the position of the engagement hole 58 of the rotor 51, is provided at the bottom wall 51A of the rotor 51. The detection target portion 57 includes a first detection target region 57A and a second detection target region 57B. The first detection target region 57A has a uniform reflectivity and an arcuate configuration with a constant width. The second detection target region 57B includes a plurality of linear portions 57Ba spaced from each other in the rotation direction of the rotor 51 and is provided adjacent to the engagement hole 58. By detecting the position of the second detection target region 57B, the position of the engagement hole 58 can be determined. By determining the position of the engagement hole 58, the position of the container holder 55 can be determined. The first and the second detection target regions 57A and 57B can be formed simultaneously by printing or applying a black paint, for example. Unlike a detection target portion in the form of a projection or a recess, the detection target portion 57 structured as described above hardly influences the balance of the center of gravity of the rotor 51. Therefore, the provision of the detection target portion 57 does not make the designing of the rotor 51 difficult.

The positioning mechanism 6 serves to locate the container 9 at a predetermined position after the centrifugal separation is finished. The positioning mechanism is made up of a detector 60, a pair of rails 35A of a table 35 and the stopper 61 in addition to the engagement hole 58 of the rotor 51.

As shown in FIG. 7, the detector 60 detects the second detection target region 57B of the detection target portion 57 based on the light reflected upon irradiation of the bottom wall 51A of the rotor 51 with light, and thereby determines the position of the engagement hole 58 and hence the position of the container holder 55 of the rotor 51. The detector 60 includes a reflective photosensor 62 and a low-pass filter 63 and is arranged to face the bottom wall 51A of the rotor 51. Specifically, the detector 60 is arranged on the upper surface 59A of a guide fin 59 fixed within the casing 50 of the centrifugal separator 5.

The reflective photosensor 62 includes a light source 64 and a light receiving portion 65. The light source 64 serves to irradiate the bottom wall 51A of the rotor 51 with light and includes e.g. an LED element. The light source 64 is capable of emitting light whose spot diameter is larger than the width of each of the linear portions 57Ba and the distance between adjacent linear portions 57Ba but smaller than the overall dimension of the second detection target region 57B. This function of the light source 64 can be achieved by appropriately selecting the kind of the light source 64 and the distance between the light source 64 and the bottom wall 51A of the rotor 51. The light receiving portion 65 receives the light reflected at the bottom wall 51A of the rotor 51 and includes e.g. a photodiode element. The low-pass filter 63 serves to remove high frequency components from the electric signals outputted from the light receiving portion 65 and is connected to an output 65A of the light receiving portion 65.

Figure 8:
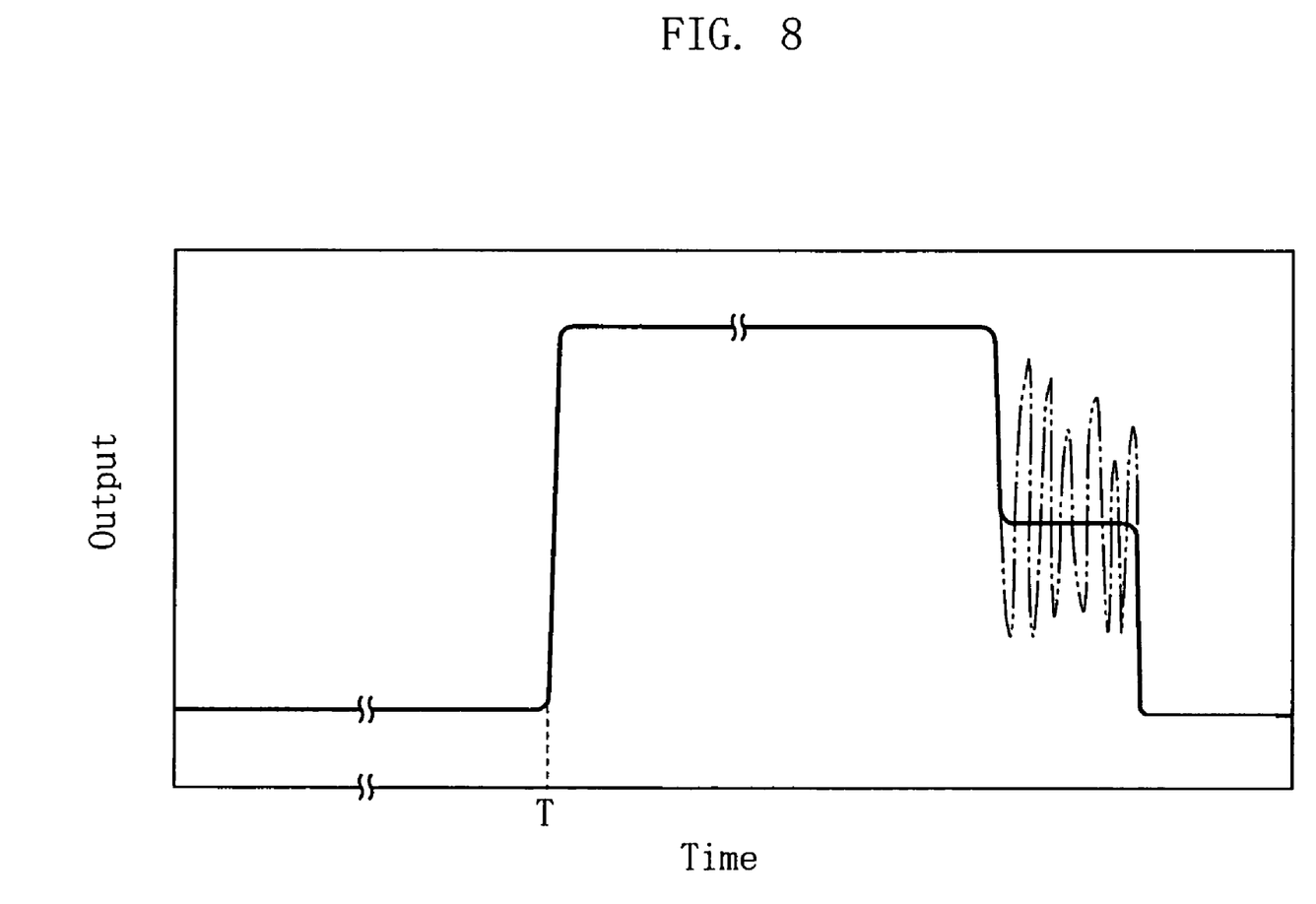
FIG. 8 is a graph showing an example of output from the light receiving portion of the detector shown in FIG. 7.

In the detector 60, as understood from FIG. 8, the light receiving portion 65 receives the smallest amount of light when the light emitted from the light source 64 impinges on the first detection target region 57A, while it receives the largest amount of light when the light impinges on portions other than the first and the second detection target regions 57A, 57B. When the light from the light source 64 impinges on the second detection target region 57B, the light receiving portion receives an intermediate amount of light. Thus, when the rotor 51 is rotated in the direction indicated by the arrow D5 in FIG. 5, the output from the light receiving portion 65 changes from a high level to an intermediate level and then to a low level repetitively. The output 65A of the light receiving portion 65 is connected to the low-pass filter 63. Therefore, even in the case where a high-frequency signal is outputted at the light receiving portion 65 when the light impinges on the second detection target region 57B (See the phantom line in FIG. 8), the low-pass filter 63 converts the high-frequency signal into a signal of an intermediate level. Accordingly, the detector 60 distinguishes the output from the low-pass filter 63 as a low level, a high level or an intermediate level and is capable of detecting the second detection target region 57B by recognizing a signal of the intermediate level.

The detector 60 further detects the number of revolutions of the rotor 51. Specifically, for example, the detector 60 detects the number of revolutions by counting the point (indicated by the reference sign T in FIG. 8) at which the output from the low-pass filter 63 changes from a low level to a high level.

As compared with the means for detecting a detection target portion by an electrical or magnetic method, the above-described detector 60 has a simpler structure and is more advantageous in terms of cost. In the detector 60, a pulse motor does not necessarily need to be utilized as the means to rotate the rotor 51, so that the size reduction of the apparatus can be easily achieved.

As shown in FIG. 3, the paired guide rails 35A are utilized for moving the stopper 61 of the positioning mechanism 6, which will be described later. Each of the guide rails 35A projects upward and includes two flat surfaces 35Aa and 35Ab which differ from each other in height and an inclined surface 35Ac connecting the flat surfaces 35Aa and 35Ab to each other.

Figure 9:
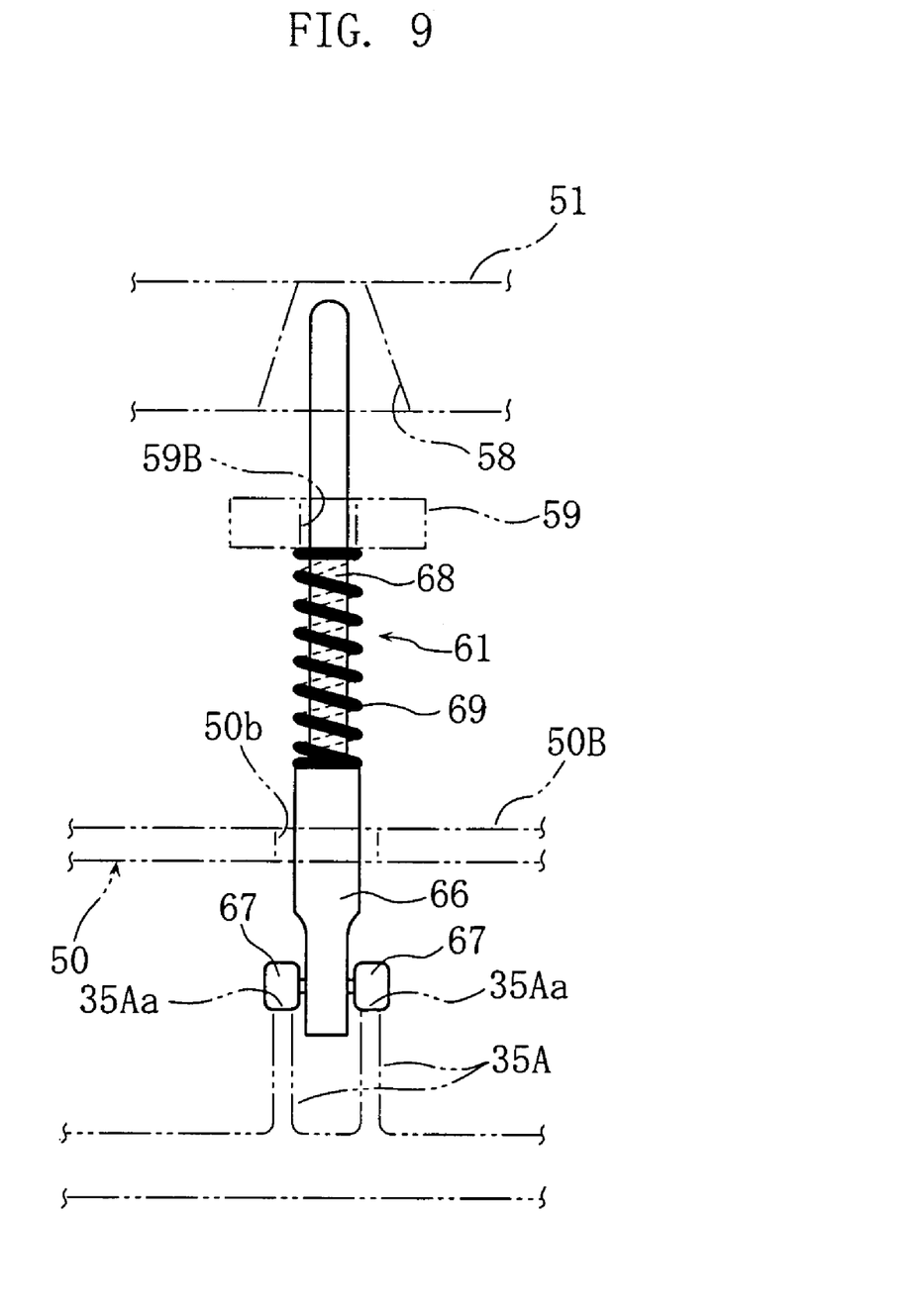
FIG. 9 is an overall side view of a stopper of a centrifugal separator.
Figure 10:
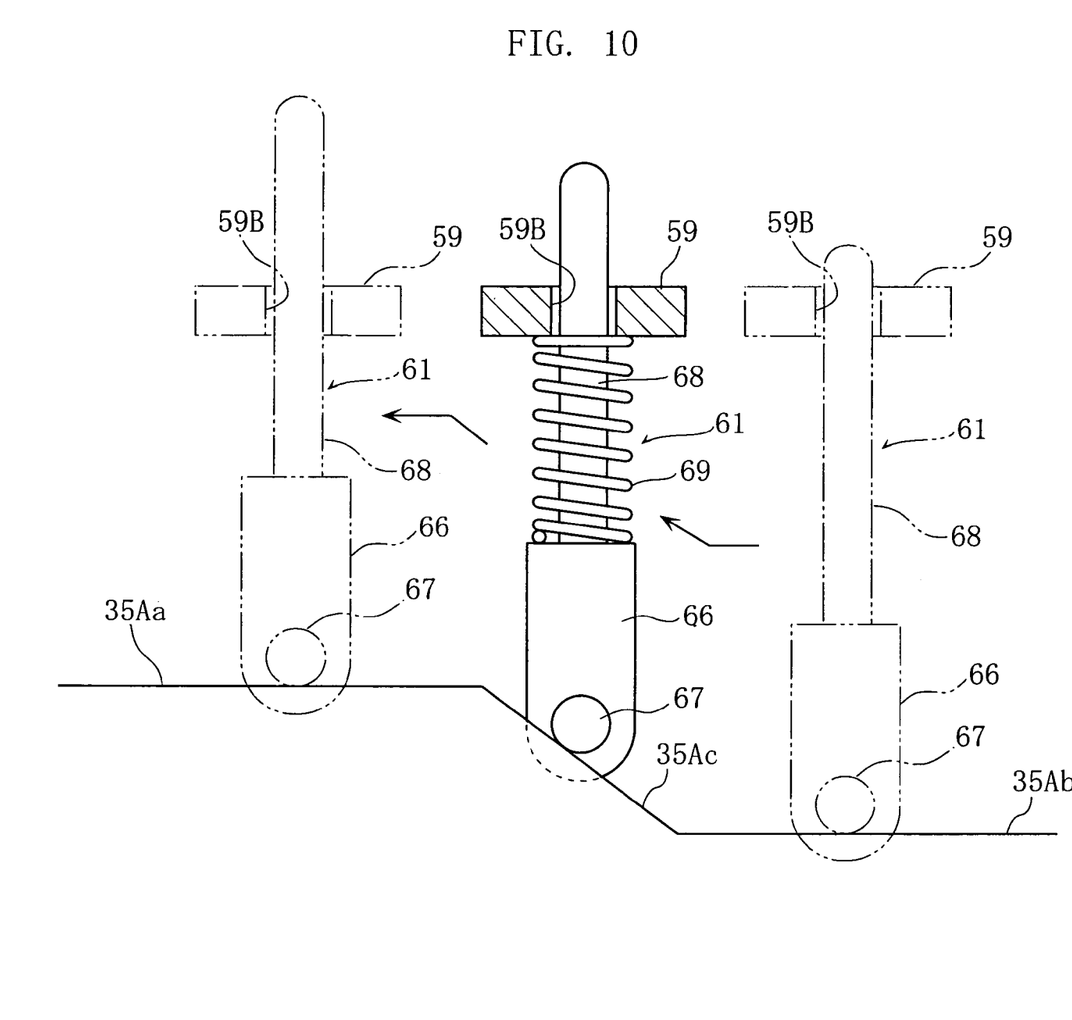
FIG. 10 is an overall front view showing the operation of the stopper.

As shown in FIGS. 9 and 10, the stopper 61 is utilized for fixing the position of the rotor 51 and movable up and down. The stopper 61 includes a support portion 66, a roller 67 and a pin 68.

The support portion 66 projects from the casing 50 through a through-hole 50b formed at the bottom wall 50B of the casing 50 of the centrifugal separator 5.

The roller 67 serves to enable the stopper 61 to move on the flat surfaces 35Aa, 35Ab and the inclined surface 35Ac of the guide rails 35A of the table 35 and is rotatably fixed to the support portion 66.

The pin 68 is inserted into the engagement hole 58 of the rotor 51 in fixing the position of the rotor 51. The pin projects upward from the support portion 66. An upper portion of the pin 68 penetrates through a through-hole 59B of the guide fin 59 fixed in the casing 50, whereas a lower portion of the pin penetrates through the through-hole 50b of the bottom wall 50B of the casing 50 so that the pin is movable up and down relative to the through-holes 50b and 59B. A coil spring 69 is arranged between the guide fin 59 and the support portion 66. Therefore, the support portion 66 is biased downward, so that the rollers 67 are held in contact with the guide rails 35A.

As described above, the stopper 61 is biased downward so that the rollers 67 are held in contact with the guide rails 35A, with the pin 68 penetrating through the through-holes 50b, 59B of the casing 50 and the guide fin 59. Therefore, when the casing 50 moves, the stopper moves together with the casing 50, with the rollers 67 rotating on the guide rails 35A. During this movement, the pin 68 moves up and down correspondingly to the height of the portion of the guide rails 35A on which the rollers 67 move. For instance, in the case where the stopper 61 moves from right to left in FIG. 10, i.e., in the case where the rollers 67 move on the guide rails 35A from the flat surface 35Ab to the inclined surface 35Ac and then to the flat surface 35Aa, the pin 68 moves upward during when the rollers 67 climb the inclined surface 35Ac. In the case where the stopper moves in the opposite direction, the pin 68 moves downward during when the rollers descend the inclined surface 35Ac. In this way, the pin 68 and the stopper 61 are movable up and down in accordance with the movement of the casing 50. The movable range of the pin is so set that the upper end of the pin 68 is positioned lower than the bottom surface of the rotor 51 when the rollers 67 are on the lower flat surfaces 35Ab and positioned higher than the bottom surface of the rotor 51 when the rollers 67 are on the upper flat surfaces 35Aa.

The engagement hole 58 of the rotor 51 is so arranged as to be positioned above the pin 68 when the second detection target region 57B of the detection target portion 57 faces the reflective photosensor 62 of the detector 60. Therefore, when the pin 68 is moved upward with the engagement hole 58 positioned above the pin 68, the end of the pin 68 is inserted into the engagement hole 58, whereby the rotor 51 is locked to stop its rotation. Since the engagement hole 58 flares downward, the insertion of the pin 68 into the engagement hole 68 can be performed relatively easily and reliably.

As shown in FIGS. 3 and 4, the pipette unit 7 serves to take the supernatant fluid (blood plasma) from the container 9 after the centrifugal separation and then apply the supernatant fluid onto the reagent pad 21A, 21B of the test piece 2A, 2B. The pipette unit is movable vertically and horizontally. The pipette unit 7 includes a nozzle 71 to which the tip 70 is to be mounted and can selectively suck air through the nozzle 71 or discharge air from the nozzle 71 by external motive power. To suck liquid into the tip 70, with the tip 70 mounted to the nozzle 71 and the air discharged from the nozzle 71, the end of the tip 70 is immersed into the liquid. In this state, by sucking air into the nozzle 71, the liquid is introduced into the tip 70. By discharging air from the nozzle 71 in this state, the liquid retained in the tip 70 is discharged.

The photometry mechanism 8 shown in FIGS. 2 and 4 serves to irradiate the reagent pad 21A, 21B of the test piece 2A, 2B with light and receive the light reflected by the reagent pad 21A, 21B. The photometry mechanism 8 includes a light emitting element and a light receiving element which are not shown. The light emitting element, which may comprise e.g. an LED lamp, emits light to irradiate the reagent pad 21A, 21B of the test piece 2A, 2B with light. The light receiving element, which may comprise e.g. a photodiode, receives light reflected by the reagent pad 21A, 21B.

The blood analysis operation using the analytical apparatus 1 will be described below.

To analyze blood by the analytical apparatus 1, the blood is first subjected to centrifugal separation to prepare a sample. The centrifugal separation of the blood is performed by setting the container 9 containing the blood to the rotor 51 and then rotating the rotor 51.

The setting of the container 9 to the rotor 51 is performed in a state in which the lid 31 of the housing 3 is opened and the centrifugal separator 5 is located in front of the housing 3. For instance, this state may be automatically achieved by pressing a predetermined operation button 32 after the lid 31 is opened. That is, by the user's operation of the button, the driving mechanism 36 operates to cause the centrifugal separator 5 to project out of the housing 3. Alternatively, the apparatus may be so designed that the centrifugal separator 5 moves automatically when the lid 31 is opened, and the test piece table 4 may be so designed as to move automatically when the centrifugal separator 5 moves. Subsequently, by bringing the shaft portions 91 of the container 9 into engagement with the cutouts 55Ae of the side walls 55Aa of the rotor 51, the container 9 is set to the rotor 51. In this state, since the cutout 55Af is provided at the lower wall 55Ad, the container 9 is held vertically along the support wall 55A of the rotor 51 without being interrupted by the lower wall 55Ad.

The rotor 51 is rotated in a state in which the centrifugal separator 5 is accommodated in the housing 3. For instance, this state may be achieved by the user by pressing a predetermined operation button 32. After the centrifugal separator 5 is accommodated in the housing 3 with the container 9 set to the rotor 51, the rotor 51 is rotated by pressing a predetermined operation button 32, for example. Alternatively, the rotor 51 may automatically start rotation when the lid 31 is closed without the pressing of the button by the user. When the rotor 51 is rotated, a centrifugal force is applied to the container 9, so that the container 9 pivots about the shaft portions 91 to become horizontal. In the horizontal state, the container 9 is surrounded by the support wall 55A, and a centrifugal force toward the bottom side of the container 9 is applied to the blood in the container 9. The blood to which the centrifugal force is applied is separated into solid components (blood cell components) and blood plasma (supernatant fluid). For instance, the rotation speed of the rotor 51 may be 8000 to 9000 rpm (1500 to 2000 G).

When the rotor 51 is rotated in this way, air flow from the center of the rotor 51 toward the outside is generated due to the action of the centrifugal force. As noted before, when the container 9 is in the horizontal state, the upper opening 90B and the periphery are surrounded by the support wall 55A (two side walls 55Aa, the deeper wall 55Ab, the upper wall 55Ac and the lower wall 55Ad). Therefore, around the container 9, air flow along the support wall 55A is generated, so that the flow of air into the upper opening 90B of the container 9 is prevented. As a result, the sample retained in the container 9 is prevented from being evaporated due to the centrifugal separation, so that undesirable change of the concentration of the sample is prevented. The air flow into the container 9 is prevented by the support wall 55A which is a structural element of the rotor 51. Therefore, it is unnecessary to provide a lid for the container 9 or positively reduce the opening diameter of the container 9 or the lid in order to prevent the air flow into the container 9. Thus, the number of parts can be reduced due to the absence of a lid. Therefore, the productivity of the container 9 can be enhanced, and the cost for the material can be reduced. Further, since the upper opening 90B of the container 9 can be made relatively large, the positioning in order to take the liquid from the container 9 by the pipette unit 7 can be rougher than in the structure in which the container is provided with a lid. Therefore, the structure of the analytical apparatus 1 can be simplified, whereby the manufacturing cost can be reduced.

Before or after the centrifugal separation, the test piece 2A, 2B is set on the test piece table 4. Specifically, the test piece 2A, 2B is set after the test piece table 4 is moved in front of the housing 3 to expose the first slit 41 and the second slits 42. Similarly to the centrifugal separator 5, this movement of the test piece table may be performed by pressing a predetermined operation button B or automatically by opening the lid 31. After the test piece 2A, 2B is set on the test piece table 4, the test piece table 4 is moved into the housing 3, and then the lid 31 is closed. The movement of the test piece plate 4 into the housing 3 is performed similarly to the centrifugal separator 5.

The test piece 2A, 2B to be set on the test piece table 4 is selected depending on the kind of a particular component to be measured. As noted before, when a plurality of kinds of components are to be measured, the test piece 2A for multi-component measurement as shown in FIG. 2 is set to the first slit 41 of the test piece table 4. On the other hand, to measure a particular component which cannot be measured by the test piece 2A for multi-component measurement or measure one of the particular components which can be measured by the test piece 2A for multi-component measurement, the test piece 2B for single-component measurement is set individually to the second slit 42.

In this embodiment, description will be given below of the measurement performed while setting only the test piece 2A for multi-component measurement. Before or after setting the container 9 and the test piece 2A, the tip 70 is set to the tip setting portion 53 of the centrifugal separator 5.

After the centrifugal separation of the blood and the setting of the test piece 2A are completed as described above, the concentration of a particular component is measured automatically. The measurement in the analytical apparatus 1 is performed by applying the supernatant fluid (blood plasma) onto the reagent pad 21A and then measuring the color development of the reagent pad 21A by an optical method.

The application of the supernatant fluid onto the reagent pad 21A is performed after the rotation of the rotor 51 is stopped in such a manner that the container holder 55 (engagement hole 58) of the rotor 51 is located at a predetermined position, and the rotor 51 is held at this position. The fixing of the rotor 51 at the position is performed by the positioning mechanism 6. The fixing of the rotor 51 by utilizing the positioning mechanism 6 includes the step of detecting the second detection target region 57B of the detection target portion 57 by the detector 60, the step of positioning the rotor 51, and the step of fixing the rotor 51.

The detection of the second detection target region 57B is performed based on the light reflected from the bottom wall 51A of the rotor 51 being continuously irradiated, with the rotor 51 intermittently turned little by little or kept turning at a low speed. Specifically, when light emitted from the light source 64 of the reflective photosensor 62 of the detector 60 is directed to the bottom wall 51A of the rotor 51, the light receiving portion 65 (low-pass filter 63) of the reflective photosensor 62 outputs signals of a high level, a low level or an intermediate level depending on the portion on which the light impinges. When the light impinges on a portion corresponding to the second detection target region 57B, a signal of an intermediate level is outputted. Thus, the detector 60 can detect the second detection target region 57B by detecting the output of a signal of an intermediate level.

The step of positioning the rotor 51 is performed by stopping the rotor 51 in a state in which the light impinges on the second detection target region 57B (in a state in which the detector 60 detects a signal of an intermediate level). When the second detection target region 57B faces the light source 64, the engagement hole 58 is positioned directly above the pin 68.

The fixing of the rotor 51 is performed by inserting the pin 68 of the stopper 61 into the engagement hole 58 of the rotor 51. Since the engagement hole 58 is positioned above the pin 68 when the second detection target region 57B faces the light source 64, the pin 68 is inserted into the engagement hole 58 by moving the pin 68 upward. The insertion of the pin 68 into the engagement hole 58 is performed by moving the centrifugal separator 5 (casing 50) in the direction of D3 by the driving mechanism 36. Specifically, when the casing 50 is moved in the direction of D3, the stopper 61 moves together with the casing 50, and the rollers 67 of the stopper 61 move on the guide rails 35A. Since the upper surface of the guide rails 35A is made up of the lower flat surface 35A$b$, the inclined surface 35A$c$ and the upper flat surface 35A$a$, the stopper 61 moves upward in accordance with the height change of the upper surface. Since the engagement hole 58 is positioned above the pin 68, the end of the pin 68 is inserted into the engagement hole 58 when the stopper 61 moves upward. As a result, the rotor 51 is locked to stop the rotation, whereby the container 9 is set at the intended position.

The application of the supernatant fluid onto the reagent pad 21A is performed by mounting the tip 70 to the nozzle 71 of the pipette unit 7 and then performing the sucking and discharging of blood plasma a number of times corresponding to the number of the reagent pads 21A to be used. Alternatively, the sucking of the blood plasma may be performed only once, and the discharging of the blood plasma may be performed a plurality of times.

The mounting of the tip 70 is performed automatically by moving the pipette unit 7 above the tip setting portion 53 provided at the casing 50 of the centrifugal separator 5 and then moving down the pipette unit 7 to insert the nozzle 71 into the tip 70.

To suck the blood plasma, with the air discharged from the nozzle 71 by external motive power, the pipette unit 7 is moved above the container 9 and then moved down to immerse the tip 70 into the supernatant fluid (blood plasma). Then, the air in the nozzle 71 is sucked by external motive power. As a result, negative pressure is generated in the tip 70 so that the supernatant fluid is sucked, whereby the blood plasma is retained in the tip 70.

To discharge the blood plasma, the pipette unit 7 is moved above the target reagent pad 21A, and then air is discharged again from the nozzle 71 by external motive force. When the blood plasma is applied onto the reagent pad 21A, the reagent contained in the reagent pad 21A reacts with the particular component in the blood plasma, and the reagent develops a color depending on the concentration of the particular component.

The photometry for checking the color development of the reagent pad 21A is performed by the photometry mechanism 8. Specifically, the photometry mechanism 8 directs light to each of the reagent pads 21A while moving the reagent pads in the direction of the arrow D2 and receives the light reflected at the reagent pad. Based on the output from the photometry mechanism 8 with respect to each of the reagent pads 21A, the degree of color development of the pad 21A, and hence the concentration of the particular component in the blood plasma is computed.

The present invention is not limited to the structure of the foregoing embodiment. For instance, the rotor of the centrifugal separator may have the structure as shown in FIGS. 11 and 12.

Figure 11A:
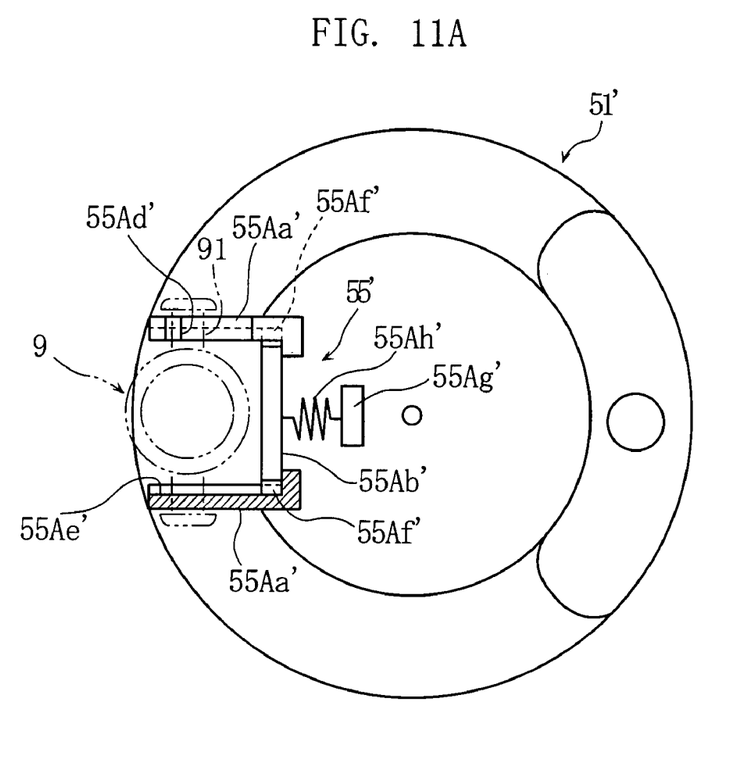
Figure 11B:
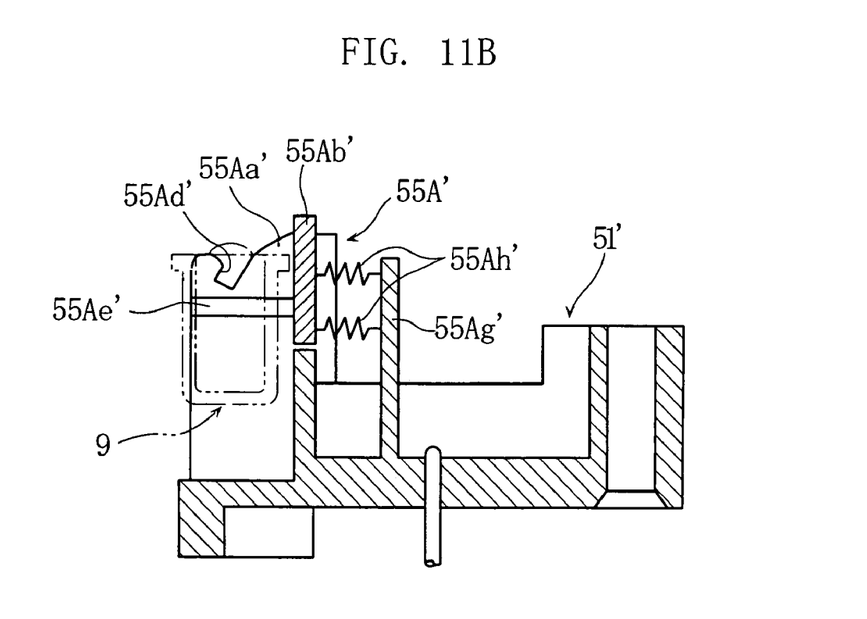
FIG. 11B is a sectional view thereof.
Figure 12A:
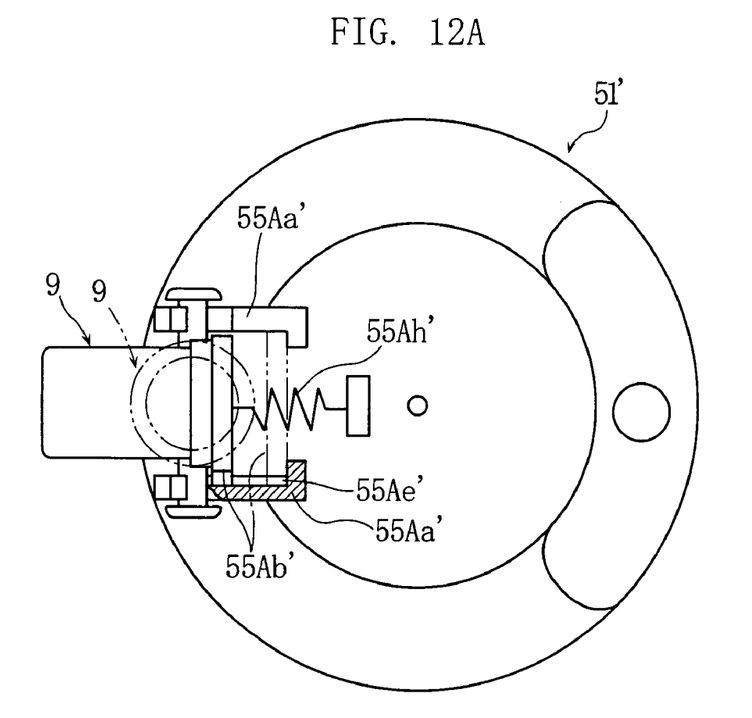

As shown in FIGS. 11A and 11B, the rotor 51' differs from the rotor 51 (See FIGS. 5 and 6) of the foregoing analytical apparatus 1 in structure of the support wall 55A'. Specifically, the support wall 55A includes two side walls 55A$a$' and a deeper wall 55A$b$', and the deeper wall 55A$b$' is movable relative to the side walls 55A$a$' in the radial direction of the rotor 51'. Each of the side walls 55A$a$' includes a cutout 55A$d$' and a groove 55A$e$'. The cutout 55A$d$' serves to receive the shaft portion 91 of the container 9. The groove 55A$e$' serves to guide the movement of the deeper wall 55A$b$' and extends generally in the radial direction of the rotor 51'. The deeper wall 55A$b$' includes two projections 55A$f$' for engagement with the respective grooves 55A$e$' of the side walls 55A$a$' and is connected to a fin 55A$g$' provided at the rotor 51' via coil springs 55A$h$'. When the rotor 51' is not rotated, the deeper wall 55A$b$' is spaced from the container 9 by a predetermined distance. As shown in FIGS. 12A and 12B, when the rotor 51' is rotated at a predetermined rotation speed, a centrifugal force is applied to the deeper wall 55A$b$'. As a result, the deeper wall 55A$b$' moves outwardly of the rotor 51' while expanding the coil springs 55A$h$' and being guided by the grooves 55A$e$' of the side walls 55A$a$'. As a result, the upper opening 90B of the container 9 is closed by the deeper wall 55A$b$'. Therefore, when the rotor 51' is rotated, air does not flow into the container 9.

Figure 12B:
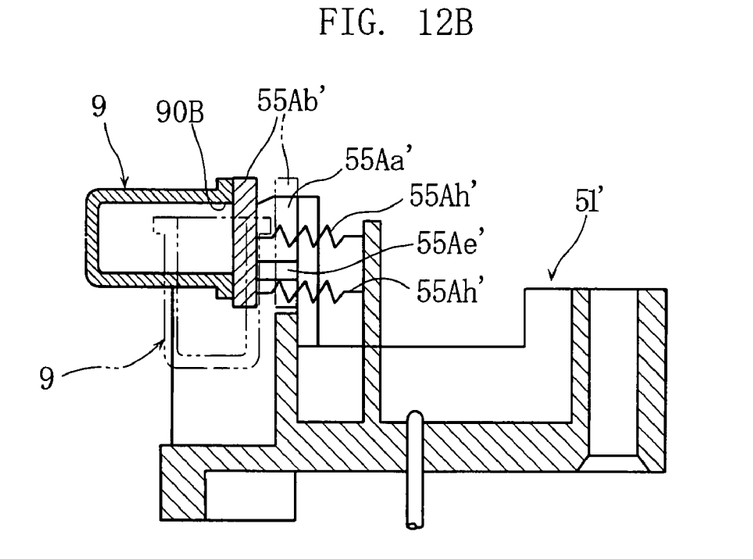
FIG. 12B is a sectional view thereof.

In the rotor 51' shown in FIGS. 11 and 12, an upper wall may be so provided as to locate on the periphery of the upper opening 90B of the container 9 when the rotor 51' is rotated. The upper wall may extend from an upper portion of the deeper wall 55A$b$' radially outwardly of the rotor 51' or bridge the two side walls 55A$a$'.

The invention claimed is:

1. A centrifugal separator comprising:
   at least one container having an upper lid-less opening; and
   a rotor which pivotally supports the at least one container, the rotor being rotated to apply a centrifugal force to the at least one container,
   wherein the rotor comprises an evaporation preventer as a structural part of the rotor, configured to prevent separation target liquid contained in the at least one container from evaporating through the lid-less opening of the at least one container when the rotor is rotated,
   wherein the evaporation preventer controls air flow around the container when the rotor supporting the container is rotated, and
   wherein the evaporation preventer includes a standing wall positioned in front of the upper lid-less opening when the container is pivoted by rotating the rotor.

2. The centrifugal separator according to claim 1, wherein the standing wall is formed integral with the rotor.

3. The centrifugal separator according to claim 1, wherein the standing wall is movable in a radial direction of the rotor.

4. The centrifugal separator according to claim 3, wherein, when the rotor is rotated, the standing wall moves outward in the radial direction due to centrifugal force.

5. The centrifugal separator according to claim 1, wherein the evaporation preventer further comprises a peripheral wall which is positioned on a periphery of the upper lid-less opening when the container is pivoted by rotating the rotor.

6. The centrifugal separator according to claim 5, wherein the peripheral wall includes an upper wall extending from an upper portion of the standing wall outward in the radial direction of the rotor.

7. The centrifugal separator according to claim 6, wherein the peripheral wall includes a lower wall positioned lower than the upper wall and extending from the standing wall outward in the radial direction of the rotor.

8. The centrifugal separator according to claim 1, wherein the evaporation preventer further comprises a pair of side walls which are positioned on a periphery of the upper lid-less opening when the container is pivoted by rotating the rotor and which project upward.

9. The centrifugal separator according to claim 8, wherein the paired side walls are connected to opposite ends of the standing wall.

10. The centrifugal separator according to claim 8, wherein each of the side walls includes an engagement portion for coming into engagement with a pivot shaft of the container in supporting the container.

11. A centrifugal separator comprising:
    at least one container having an upper lid-less opening; and
    a rotor which pivotally supports the at least one container, the rotor being rotated to apply a centrifugal force to the at least one container,
    wherein the rotor comprises an evaporation preventer as a structural part of the rotor, configured to prevent separation target liquid contained in the at least one container from evaporating through the lid-less opening of the at least one container when the rotor is rotated,
    wherein the rotor is configured to support one container and has a center of gravity which is offset from a rotation axis of the rotor when the rotor is not supporting the container, and
    wherein a center of gravity of the rotor and the container in combination is located on the rotation axis when the rotor is rotated at a predetermined rotation speed, with a predetermined amount of separation target liquid retained in the container, so that the container is pivoted through a predetermined angle.

12. An analytical apparatus for analyzing at least one component contained in a sample, the analytical apparatus comprising a centrifugal separator for separating a solid component contained in the sample from a liquid component, wherein the centrifugal separator includes:
    at least one container having an upper lid-less opening; and
    a rotor which pivotally supports the at least one container, the rotor being rotated to apply a centrifugal force to the at least one container,
    wherein the rotor comprises an evaporation preventer as a structural part of the rotor, configured to prevent separation target liquid contained in the at least one container from evaporating through the lid-less opening of the at least one container when the rotor is rotated,
    wherein the evaporation preventer controls air flow around the container when the rotor supporting the container is rotated, and wherein the evaporation preventer includes a standing wall positioned in front of the upper lid-less opening when the container is pivoted by rotating the rotor.

13. The analytical apparatus according to claim 12, wherein the standing wall is integrally formed on the rotor.

14. The analytical apparatus according to claim 12, wherein the standing wall is movable in a radial direction of the rotor.

15. The analytical apparatus according to claim 14, wherein, when the rotor is rotated, the standing wall moves outward in the radial direction due to a centrifugal force.

16. The analytical apparatus according to claim 12, wherein the evaporation preventer further comprises a peripheral wall which is positioned on a periphery of the upper lid-less opening when the container is pivoted by rotating the rotor.

17. The analytical apparatus according to claim 16, wherein the peripheral wall includes an upper wall extending from an upper portion of the standing wall outward in the radial direction of the rotor.

18. The analytical apparatus according to claim 17, wherein the peripheral wall includes a lower wall positioned lower than the upper wall and extending from the standing wall outward in the radial direction of the rotor.

19. The analytical apparatus according to claim 12, wherein the evaporation preventer further comprises a pair of side walls which are positioned on a periphery of the upper lid-less opening when the container is pivoted by rotating the rotor and which project upward.

20. The centrifugal separator according to claim 19, wherein the paired side walls are connected to opposite ends of the standing wall.

21. The analytical apparatus according to claim 20, wherein each of the side walls includes an engagement portion for coming into engagement with a pivot shaft of the container in supporting the container.

22. An analytical apparatus for analyzing at least one component contained in a sample, the analytical apparatus comprising a centrifugal separator for separating a solid component contained in the sample from a liquid component, wherein the centrifugal separator includes:
at least one container having an upper lid-less opening; and
a rotor which pivotally supports the at least one container, the rotor being rotated to apply a centrifugal force to the at least one container,
wherein the rotor comprises an evaporation preventer as a structural part of the rotor, configured to prevent separation target liquid contained in the at least one container from evaporating through the lid-less opening of the at least one container when the rotor is rotated,
wherein the rotor is capable of supporting a container and has a center of gravity which is offset from a rotation axis of the rotor when the rotor is not supporting the container, and
wherein a center of gravity of the rotor and the container in combination is located on the rotation axis when the rotor is rotated at a predetermined rotation speed, with a predetermined amount of separation target liquid retained in the container, so that the container is pivoted through a predetermined angle.

* * * * *